United States Patent [19]

Jackson

[11] Patent Number: 4,547,195
[45] Date of Patent: Oct. 15, 1985

[54] SANITARY NAPKIN WITH MALODOR COUNTERACTANT MEANS

[75] Inventor: David M. Jackson, Gwinnett County, Ga.

[73] Assignee: Kimberly-Clark Corporation, Neenah, Wis.

[21] Appl. No.: 401,483

[22] Filed: Jul. 26, 1982

[51] Int. Cl.⁴ .............................................. A61F 13/16
[52] U.S. Cl. .................................................... 604/359
[58] Field of Search .................................. 604/359, 385

[56] References Cited

U.S. PATENT DOCUMENTS

| | | | |
|---|---|---|---|
| 2,418,907 | 4/1947 | Schreiber | 604/359 |
| 3,732,867 | 5/1973 | Money | 604/359 |
| 3,856,014 | 12/1974 | Yamauchi | 604/359 |
| 3,926,189 | 12/1975 | Taylor | 604/359 |
| 3,954,107 | 5/1976 | Chesky et al. | 604/385 |
| 4,055,184 | 10/1977 | Karami | 604/359 |
| 4,195,634 | 4/1980 | DiSalvo et al. | 604/359 |
| 4,363,322 | 12/1982 | Andersson | 604/359 |

FOREIGN PATENT DOCUMENTS 569380  5/1945  United Kingdom ............... 604/359

*Primary Examiner*—John D. Yasko
*Attorney, Agent, or Firm*—James P. O'Shaughnessy

[57] ABSTRACT

A sanitary napkin having an absorbent batt which is folded along each longitudinal edge is provided. Malodor counteractant means are positioned between the folded absorbent layers.

3 Claims, 1 Drawing Figure

SANITARY NAPKIN WITH MALODOR COUNTERACTANT MEANS

FIELD OF THE INVENTION

The subject invention relates to a sanitary napkin and particularly one having malodor counteractant means.

BACKGROUND OF THE INVENTION

It has been recognized that menses contain malodorous compounds and that these compounds are objectionable to menstruating women. Attempts to minimize the effects of these compounds have been directed towards incorporating odor absorbents such as bicarbonate or activated charcoal in sanitary napkins or, in the alternative, adding masking agents such as perfume to hide the unpleasant odors associated with menses discharge.

When perfumes are used, they have a tendency to dissipate rapidly if applied in some manner to an exposed surface. Various attempts have been made to place perfumes in microcapsules within the garment attachment adhesive line so that when the release paper is removed the microcapsules rupture liberating the fragrance. This particular approach is exotic from the manufacturing standpoint and also may interfere with the necessary adhesive properties desirable for sanitary napkin attachment to the wearer's undergarment.

U.S. Pat. No. 4,237,591 describes the concept of introducing perfumes along an impregnated cellulosic string which is placed into the absorbent batt as the batt is formed. This complicated process is designed to utilize the thickness of the absorbent batt as a means for delaying the premature release of fragrance. This process, however, requires an additional element which must be placed carefully within the batt during the manufacturing operation.

SUMMARY OF THE INVENTION

This invention relates to a sanitary napkin having an absorbent which is folded along each of its longitudinal edges and has malodor counteractant means positioned in at least one of the folds.

This invention has several advantages. A sanitary napkin can be provided with a variety of perfume-like masking agents which could not otherwise be utilized due to their volatility or potential for skin irritation. Also, precise levels of perfume can be readily applied in precise patterns without unduly complicating the manufacturing step. Also, the napkin itself will serve as a delay mechanism due to the thickness of the absorbent in the folded area to prevent premature release of these masking components.

DETAILED DESCRIPTION OF THE INVENTION

Figure 1:
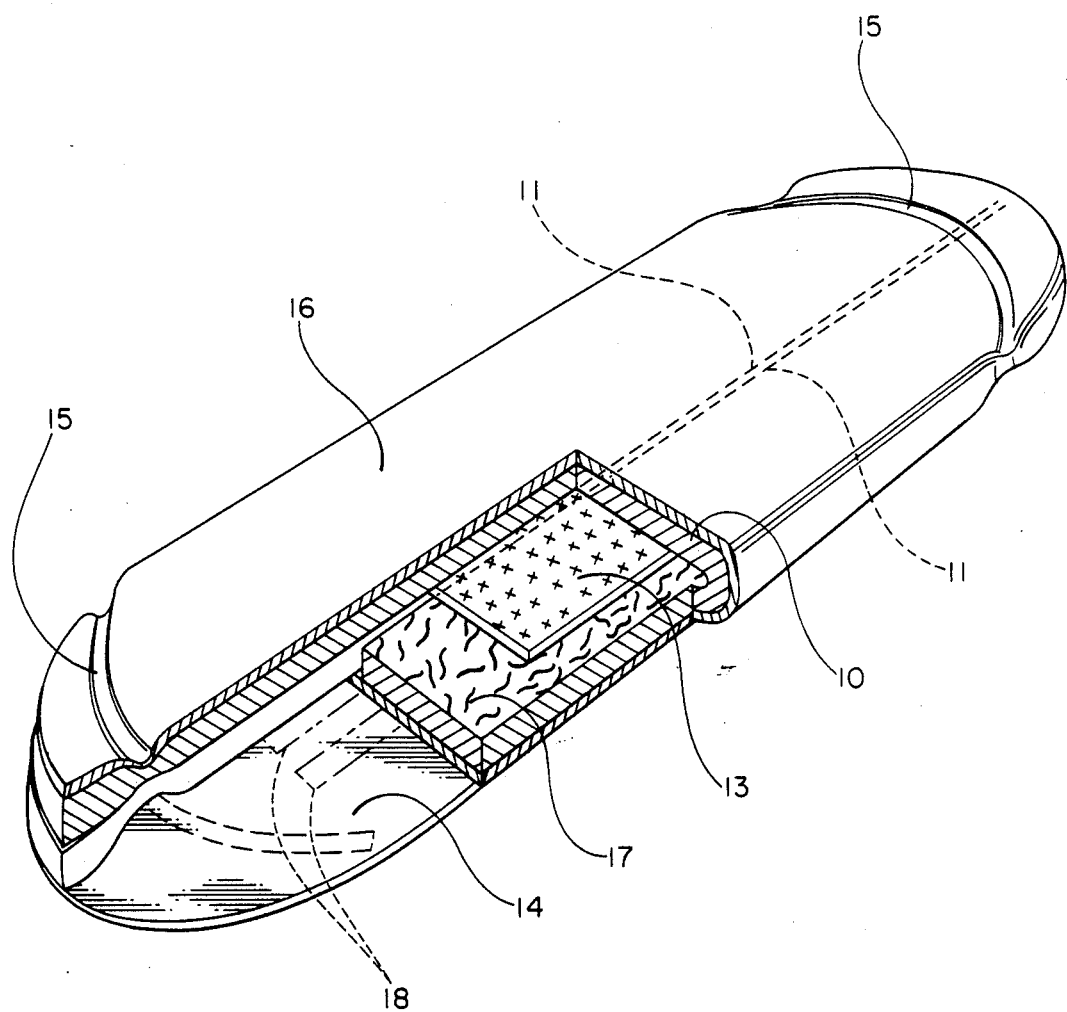

This invention can be more readily understood by reference to the drawing in which FIG. 1 is a cross-sectional view of a preferred embodiment of the napkin of this invention.

This can be seen in FIG. 1, an absorbent layer 10 is surrounded by fluid permeable wrap 16 which is folded underneath itself to form closely adjacent edges shown in phantom lines 11. The malodor counteractant shown as sinuous line 17 is positioned to be preferably most dense in concentration near the folded portion of the absorbent 10. It is in fact not necessary that the absorbent edges abut each other on the bottom portion as shown by dotted lines 11 but this may be done for purposes of uniformity.

In this particularly preferred embodiment, an intermediate layer of a superabsorbent material 13 is also positioned within the confines of the folded layer of the absorbent component 10. By enhancing the fluid concentration near the sites of malodor counteracting agent 17 it is felt that the efficiency of malodor counteraction can be enhanced. As can be seen from the drawing, it is generally preferred to position the majority of the malodor counteractant components on the top of the bottom surface of absorbent 10, but the malodor counteractant could as easily be positioned on the bottom of the top of the folded absorbent layer. As is conventional a fluid permeable baffle 14 is adhesively attached to the bottom of the folded absorbent layer. The napkin is held in place in the undergarment by parallel adhesive attachment strips shown by phantom line 18. The transverse ends of the absorbent layer 10 are not sealed at the ends but instead are sealed at bands 15 somewhat inset from the ends. Preferably the sealing is accomplished by fusing but sealing can also be by adhesive means. The cover material 16 is a nonwoven thermoplastic wrap which can easily be fused to the remaining components of the napkin at the bands 15.

The process for practicing this invention really involves the steps of forming a batt of absorbent material the batt being designed to be folded on each of its longitudinal edges adding the malodor counteractant material at a portion of the batt which will be within the folded area folding the batt and attaching a fluid impermeable baffle to the folded section. Obviously, in the preferred embodiment, the superabsorbent or other absorbent enhancement material can be added in a thin strip within the confines of the folded area prior to the fold. Also, as another variant, a fluid previous wrap can be used as a carrier for the absorbent batt and, if this process step is used, the baffle will be attached to the portion of the fluid previous cover overlying the bottom of the folded absorbent. Alternatively, the wrap will encircle both the folded absorbent and the baffle and the garment attachment adhesive will be used to seal the overlapped portions of the wrap as well as provide for garment attachment.

The term malodor counteractant as used within the specification relates generally not only to masking fragrances but also to odor absorbent means such as activated charcoal bicarbonate of soda, etc. If the odor absorbent means are positioned in conjunction with an absorbent enhancement layer in the middle of the napkin, the efficacy of odor absorbency can be enhanced.

What is claimed is:

1. A sanitary napkin comprising a folded absorbent batt as the major absorbent component of said napkin, a fluid impermeable baffle attached to one outer surface of said batt and a fluid previous cover attached to the other outer surfaces of said batt, said absorbent batt having a malodor counteractant means disposed in at least one of said folds.

2. The sanitary napkin according to claim 1 wherein an absorbent enhancement layer is positioned within the folded portion of the absorbent batt.

3. The sanitary napkin according to claim 1 wherein the malodor counteractant means is a masking scent.

* * * * *